(12) United States Patent
Pietilainen

(10) Patent No.: US 6,726,808 B1
(45) Date of Patent: Apr. 27, 2004

(54) METHOD FOR DETERMINATION OF THE CHARGING STATE FOR FILTRATES OF MASSES IN PAPER AND BOARD MACHINES

(76) Inventor: Erkki Pietilainen, Frilundintie 5 C 20, Fin-65170 Vaasa (FI)

( * ) Notice: Subject to any disclaimer, the term of this patent is extended or adjusted under 35 U.S.C. 154(b) by 0 days.

(21) Appl. No.: 09/868,472

(22) PCT Filed: Dec. 17, 1999

(86) PCT No.: PCT/FI99/01052

§ 371 (c)(1),
(2), (4) Date: Sep. 27, 2001

(87) PCT Pub. No.: WO00/37922

PCT Pub. Date: Jun. 29, 2000

(30) Foreign Application Priority Data

Dec. 18, 1998 (FI) .................................................. 991963

(51) Int. Cl.$^7$ ................................................. D21F 13/00
(52) U.S. Cl. ....................... 162/198; 356/300; 356/303; 356/319; 356/320
(58) Field of Search .......................... 162/198; 356/300, 356/303, 319, 320, 321, 322, 323, 324, 325, 326, 327, 328

(56) References Cited

U.S. PATENT DOCUMENTS

| | | | |
|---|---|---|---|
| 4,403,032 A | * 9/1983 | Zeikus et al. | 435/18 |
| 4,780,182 A | * 10/1988 | Baker | 162/49 |
| 6,398,914 B1 | * 6/2002 | Furumoto | 162/198 |

* cited by examiner

*Primary Examiner*—Peter Chin
(74) *Attorney, Agent, or Firm*—Rolf Fasth; Fasth Law Offices

(57) ABSTRACT

The invention is concerned with a method for the determination of the charging state of filtrates of fiber masses used in the manufacturing of paper and cardboard. In the method, a sample is filtrated from fibers through a filter, and indicator color is added to the filtrate. The absorbance of the filtrate is measured and the charging state of the solution is read from an earlier made calibration curve that corresponds to the measured absorbance. In the first embodiment of the invention, the calibration curve is made by taking a sufficient amount of samples from the same anionic sample and such different known amounts of cationic agent are added to these samples, that at least a part of the samples are cationic and at least a part of the samples are anionic. The charging states of the filtrated samples are determined in a previously known way, e.g. by cationic titration or potentiometric measurements, whereafter the absorbances corresponding to the charging states are measured, and a calibration curve or table is drawn, wherein a given absorbance corresponds to a given charging state.

9 Claims, 4 Drawing Sheets

Figure 1:
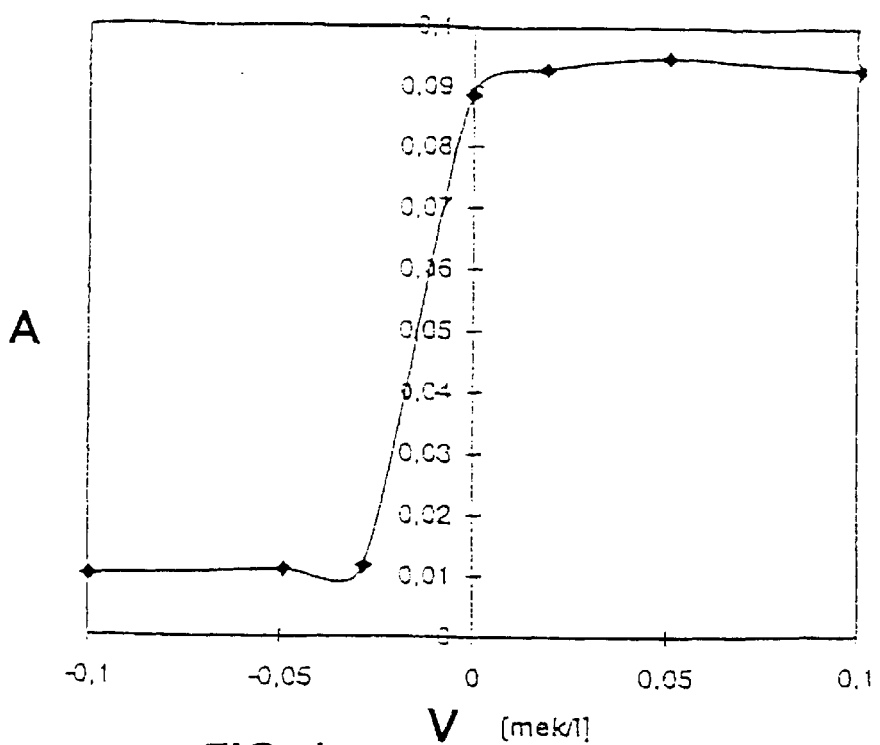

METHOD FOR DETERMINATION OF THE CHARGING STATE FOR FILTRATES OF MASSES IN PAPER AND BOARD MACHINES

TECHNICAL FIELD

The invention is concerned with a method for determination of the charging state for filtrates of fiber masses used for manufacturing of paper and cardboard.

BACKGROUND ART

The amount of harmful substances are followed up at paper and board machines by determination of the charging state of the colloidal filtrates of fiber masses used for manufacturing of paper and cardboard. The reason for the adjusting of the charging states is that the harmful colloidal substances contained in those would be possible to adjust to improve the functioning of the machines. Conventional methods are based on colloidal titration or potentiometric measurements, directly on the filtrated sample. In such a method, an indicator and a cationic reagent is added to the filtrated sample and also to a water amount representing a reference. After that, the equivalent points of the reference and the sample are determined by titration with an anionic agent. The charging state of the sample is calculated on the basis of the consumption of the anionic agent by comparing with the 0-sample (the reference).

The disadvantage with such a method is that it is slow an unpractical and that the colloidal solutions adhere to the measurement equipment.

The object of this method is to develop a quick and precise method, which does not have the disadvantages of the previous methods.

Especially, the object of this invention is to develop a method, with which the measurement of the charging state would be easy to carry out without any troublesome titration.

SUMMARY OF THE INVENTION

The method of the invention is mainly characterized in that, the sample is filtrated out from fibers through a filter and indicator color is added to the filtrate in solid state or as a liquid. Thereafter, the absorbance of the filtrate is measured and the charging state of the solution is read from the corresponding place of a previously made calibration curve.

In the construction of the calibration curve, a sufficient amount of samples are taken from the same anionic sample and such different known amounts of cationic agent are added to these samples that at least a part of the samples are cationic and at least a part of the samples are anionic. With the term sufficient amount, it is meant that a sufficient amount of points are achieved to be able to draw a calibration curve. Some kind of a calibration curve can already be drawn with 5–6 samples, but ca 10 samples are needed to achieve an exact curve. The charging states of the filtrated samples are determined in previously known manner, e.g. by cationic titration or by potentiometric measurements. Thereafter, the absorbances corresponding to the charging states of the samples are measured, and a calibration curve is drawn, wherein a given absorbance corresponds to a given charging state. The equivalent point can also be determined mathematically without a drawn curve.

In alternative, the calibration curve can be made so that a sufficient amount of samples are taken from the same anionic sample and such different amounts of cationic agent are added to these samples so that at least a part of the samples are cationic and a part are anionic, after which the same amount of cationic agent is added to all the samples so that all the samples are cationic. The charging states of the filtrated samples are then determined in a previously known way, e.g. by anionic titration, after which the charging states of the samples and the corresponding absorbances are measured. The calibration curve is drawn as above, wherein a given absorbance corresponds to a given charging state.

The absorbance is measured at a wave length, which is within the range of the visual light and at which the indicator absorbs. This most clearly takes place at the wave length of 500 or 615 nm, most preferably the wave length of 615 nm is used. The absorbance is measured with a spectrophotometer.

The indicator is for example p-toluidin or a corresponding indicator that change color when the charging state changes. The amount of the indicator is such that the change of the color during the titration is visible with the bare eye.

The object for the measurement is a filtrate of a mass used as raw material for paper or cardboard, a filtrate of coated reject or some other fiber mass filtrate used in connection with paper manufacturing.

The filtration is performed with a black band filter paper or the like, with which fibers can be filtered out.

The cationic agent is a cationic polymer, polydadmac™ or the like.

The invention is described in more detail in the following in connection with advantageous principle examples and embodiment examples. The invention is not restricted to the details of the examples.

Thus, in the invention, there is made use of the fact that the absorbance of the solution is strongly increased at a certain wave length of light transmitted through the sample, especially at the equivalent point, when a cationic regent is added to the anionic solution, and there is used indicator in the titration, e.g. p-toluidin, added to the solution.

The invention has several advantages compared to the known colloidal titration method. It can especially be mentioned that it is quick and easy to carry out. A practical advantage is that the vessels and tools used, such as cuvettes and mixers etc. stay clean.

The invention can be used as a component of an automatic continuously working measuremtn device of for the measurement of paper processes, also for the cardboard and cellulose industry.

EMBODIMENT EXAMPLE 1

The Performance of the Colloidal Titration
0-sample:
 5 ml sample of distilled water or some other practical amount is taken. The 5 ml sample is added to 50 ml of diluted indicator, e.g. a p-toluidin solution. 5 ml of diluted polydadmac solution or some other cationic reagent is added. The equivalent point is determined by titration with diluted potassium polyvinyl sulfate or a corresponding anionic agent, until the color of the solution is permanently changed. The result=A ml.
Titration of the sample:
 The sample is titrated in the same way as the zero sample, but instead of distilled water there is used a filtrate of reject or some other fiber mass used in the manufacturing of paper. The filtration takes place through a conventional filter paper used in laboratories.

Calculation of the result:
  The result is achieved from the following formula:

$$\frac{A \text{ ml} - B \text{ ml}}{5 \text{ ml}} \text{ meq/ml } ( = \text{milliequivalents/liter})$$

A and B was determined above and the result is the consumption of anionic agent per sample compared to the consumption of distilled water.

The effect of solid matters can be eliminated before the color addition and by subtracting this result from the final result. Modern apparatuses can do this automatically. Also the effect of the dilution can be eliminated by using more concentrated solutions or by programming the devices to take the dilution into consideration in the calculations.

EMBODIMENT EXAMPLE 2

Calibration

First, the titration curve is constructed. For example 5 ml of anionic filtrate of a mass used as raw material for paper is taken. The filtration can be carried out with an ordinary black band filter paper or the like. The sample is placed in a cuvette of a calorimeter (spectrophotometer) and 50 ml of diluted p-toluidin indicator color is added during continuous mixing. The absorbance of the solution is measured at a wave length of 615 nm (which is the wave length, at which the indicator absorbs best) of the light going through the sample. Cationic polymer, diluted polydadmac or the like is added. After each addition, it is waited until the titration reaction is ended before the absorption is measured with a calorimeter.

A titration curve is thus obtained, wherein the change of the charging state can be seen as a change in the absorption.

The titration curve can also be constructed with so called "back titration", i.e. the sample is first made cationic with known amounts of reagent followed by titration as above, but with anionic agent as titration solution. Next, the absorption readings corresponding to given charging states are calibrated on the titration curve.

Ca two dl of the same fiber mass is put in a sufficient amount of decanter glasses. Diluted polydadmac or some other cationic polymer is added until 1% in such a way that the first sample contains a half kilogram of polymer per 1000 kg dry matter, the next contains a kilogram, then one and a half and so on and then it is stirred. The fixing agent, i.e. the cationic polymer, is allowed to effect for 10 min, after which filtration is carried out as above. The intention is that a part of the samples would be anionic and a part of the samples cationic. It does not matter if some sample would be neutral.

The charging state of the five milliliter samples taken from the filtrates is determined with colloidal titration. After that, five milliliters are taken from each sample and mixed with 50 ml diluted indicator color. The absorbances corresponding to the charging states of the samples are measured with a calorimeter and are placed on the titration curve formed above. The relation between the absorbance achieved and the charging state thus obtained can be used in the determination of the charging state of the reject samples without titration, directly colorimetrically.

An own calibration has to be made for each type of mass, as the impurities of the masses might have a negative influence on the results. In other words, it is not possible to read the charging states of the filtrates of groundwood pulp from a calibration curve made for a reject filtrate.

The effects of solid particles on the absorption can be corrected by measuring the absorption of the filtrated samples before the addition of color reagent and by subtracting the error caused by the opacity from the absorbance reading.

EMBODIMENT EXAMPLE 3

Measurement

The charging state of coated reject is wanted.

A five milliliter sample is taken from the filtrate and is mixed with 50 ml diluted indicator color. The absorbance of the solution is measured at the wave length of 615 nm with a calorimeter and the charging state is read from the corresponding place of the titration curve.

In the following some advantageous examples of the invention are presented. The intention is not to restrict the invention to the details of the examples.

EXAMPLE 1

Water Solution

Absorbance measurements were performed for a water solution containing only anionic and cationic reagent and indicator. The test was performed in the following way: The anionicity of the water was adjusted to the level 0.1 meq/l with PPVS (potassiumpolyvinylsulfate) and a indicator water solution was added. The charging state was adjusted for the different samples by adding MGC (methylglycolochitosane) in such a way that, there were obtained six samples with charging states within the range of −0.1–0.1 meq/l. The absorbances of the samples were measured at the wave length 615 nm, which has shown to be the wave length range, wherein the absorbance most marked changes when the charging state changes. FIG. 1 shows the relation between the charging state and the absorbance in such a water solution. The change is very clear and stepwise from one absorbance level to another at the equivalent point.

FIG. 1: Absorbance vs charging state in a water solution containing anionic and cationic reagent and indicator color. In the figure A=absorbance and V=charging state.

EXAMPLE 2

Groundwood Pulp

The colloidal titration gave an anionicity of the filtrate of the groundwood pulp of 0,.14 meq/l. In spite of the clear anionicity, the addition of indicator water solution did not give any visible color change. PPSV was added to the sample in such a way that the anionicity was 0.3 meq/l and a clear color change was achieved. From the sample treated in this way, samples were made for the absorbance measurements by titration with MGC. The effect of the charging state with respect to the absorbance can be seen in FIG. 2.

Figure 2:
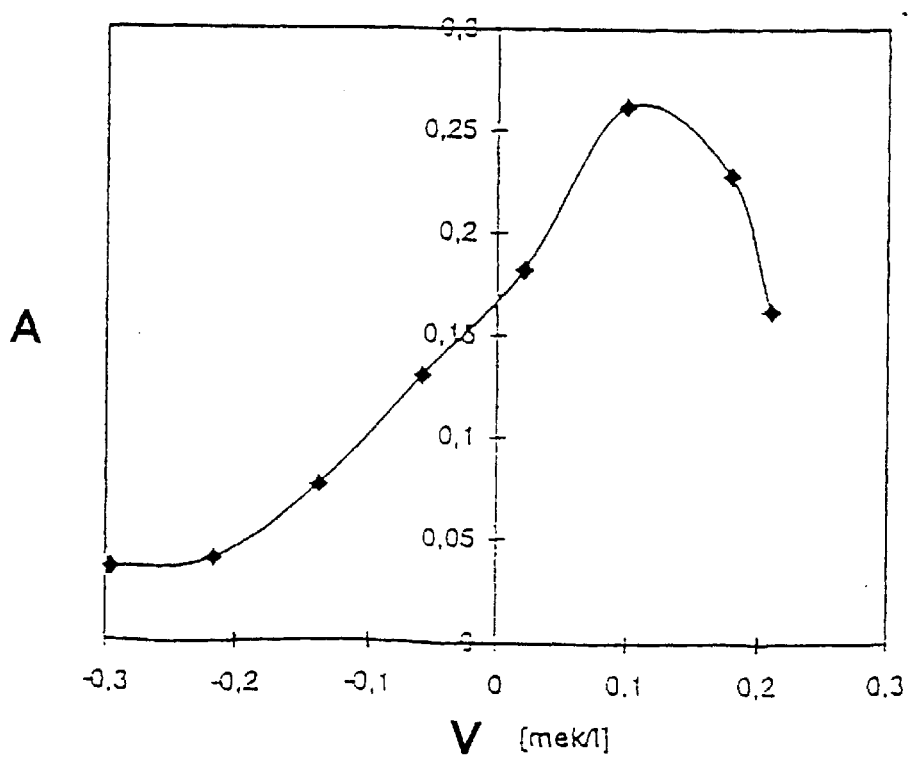

FIG. 2: The effect of the charging state on the absorbance of groundwood pulp.

Different amounts of MGC were added to the groundwood pulp for comparison. Filtrates were made form the masses. The charging state and absorbance (with indicator color) of the filtrates were measured. The curve thus obtained is presented in FIG. 3. FIG. 4 presents both curves of the groundwood pulp.

Figure 3:
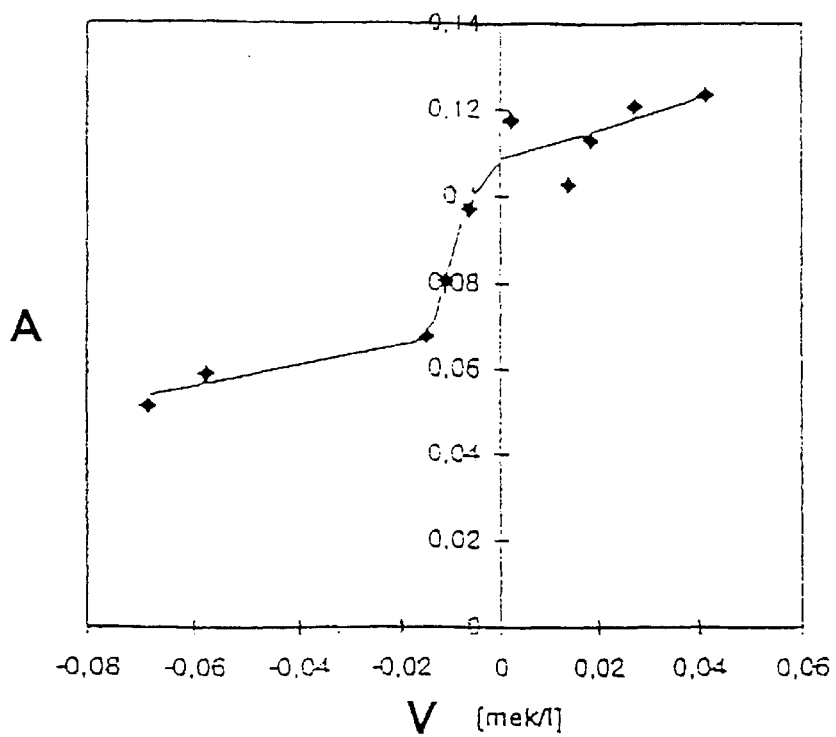
Figure 4:
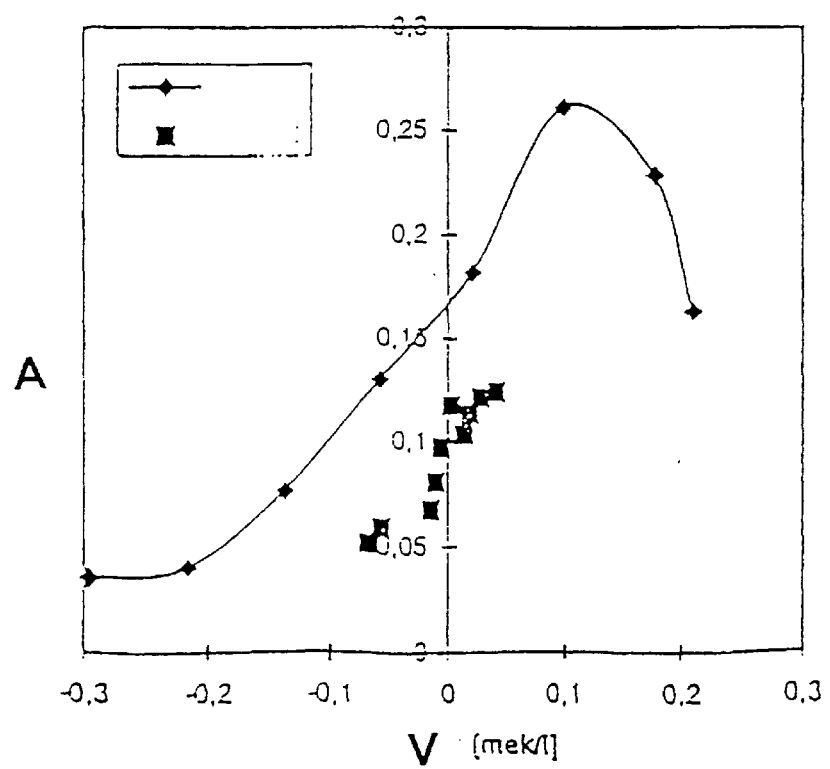

FIG. 3. The absorbance obtained from the comparison sample made from groundwood pulp. The upper curve is made from the filtrate, the lower points are made from the comparison sample.

FIG. 4. Curves made from the filtrate and comparison sample from groundwood pulp.

In the comparison filtrate, the absorbances were in a corresponding charging state at a lower level than the absorbance of the samples made from the filtrate by titration. This might for example depend on flocculation of the colloidal matter and small particles when cationic agent is added to the fibers, whereby a clearer filtrate, which allows more light to pass is obtained, which naturally has an influence on the "basic level" of the absorbance.

EXAMPLE 3

Coated Reject

Figure 5:
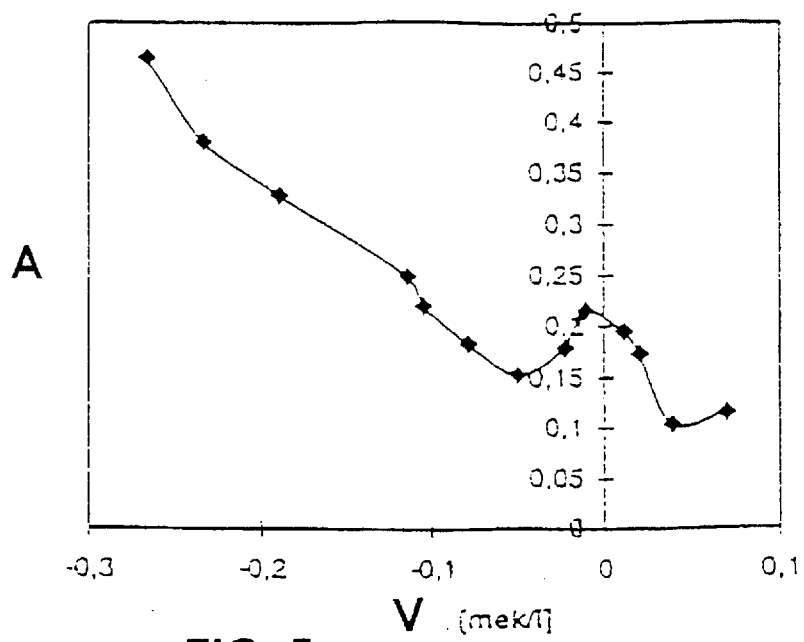

The charge of a sample of coated reject was also too low for the color change reaction. To increase the anionicity, coating paste was added to the sample, by means of which the anionicity of the filtrate made from the sample became 0.6 meq/l. The same tests were made for the filtrate as for the groundwood pulp. FIG. 5 presents the effect of the charging state of the filtrate in different charging states.

FIG. 5. The absorbance of the reject sample vs. the charging state. The upper curve is made on the first day. The lower curve is made on the following day.

Figure 6:
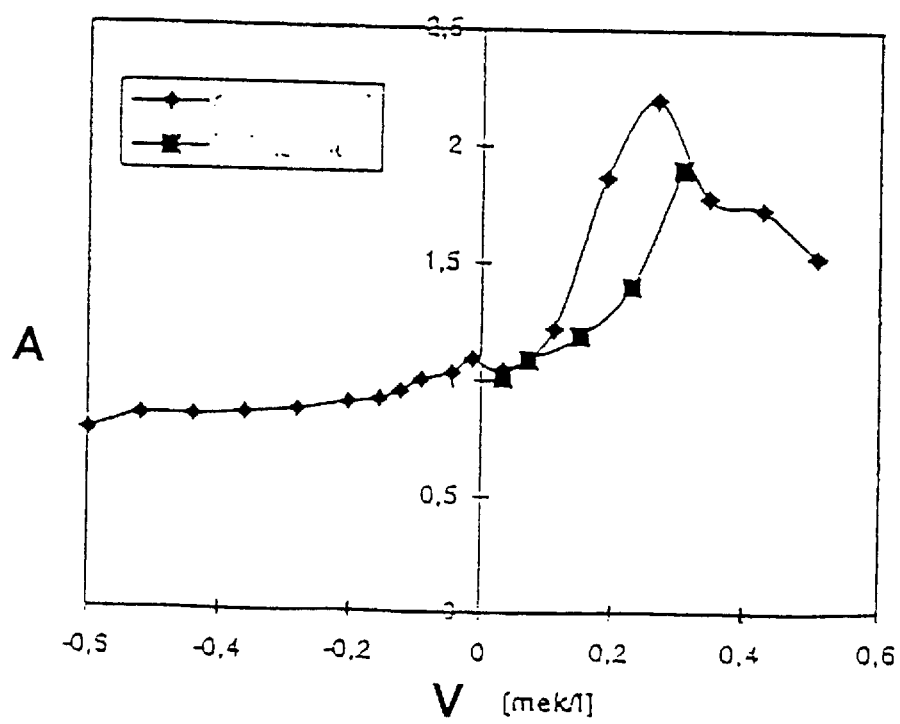
Figure 7:
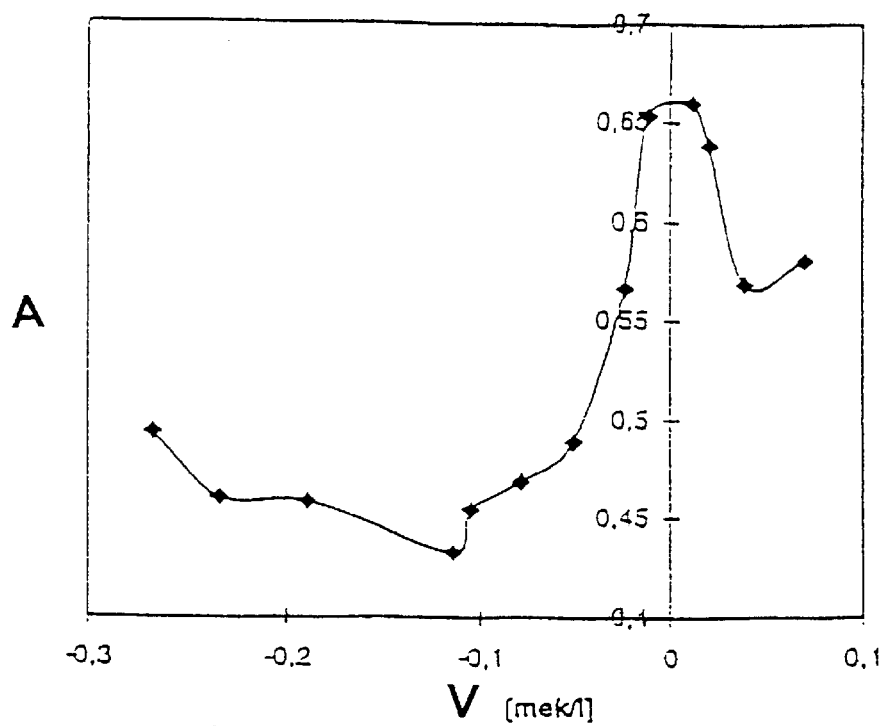

FIG. 6 presents in the same way the absorbance vs. the charging state obtained from the comparison sample. The most important factor for the continuously decreasing absorbance after the additions of MGC is the dilution of the sample. The change of the charging state by adding cationic reagent to the mass requires big amounts of reagent, whereby the sample is considerably diluted. In the last point, the dilution was as much as 1.7 folded. Also the possible colloidal flocculation mentioned above might have an influence on the form of the curve. The more anionic the filtrate is, the more easy the colloids stay in a dispersed state and the more opaque is the solution. Coagulation takes place at the equivalent point and the particles strive to move to the bottom. In FIG. 7, the effect of the dilution has been tried to compensate for, and in FIG. 8, both curves are place in the same coordinate system.

FIG. 6. The absorbance vs. charging state of the comparison sample.

FIG. 7. The absorbance vs. charging state of the comparison sample when the error due to dilution has been compensated.

Figure 8:
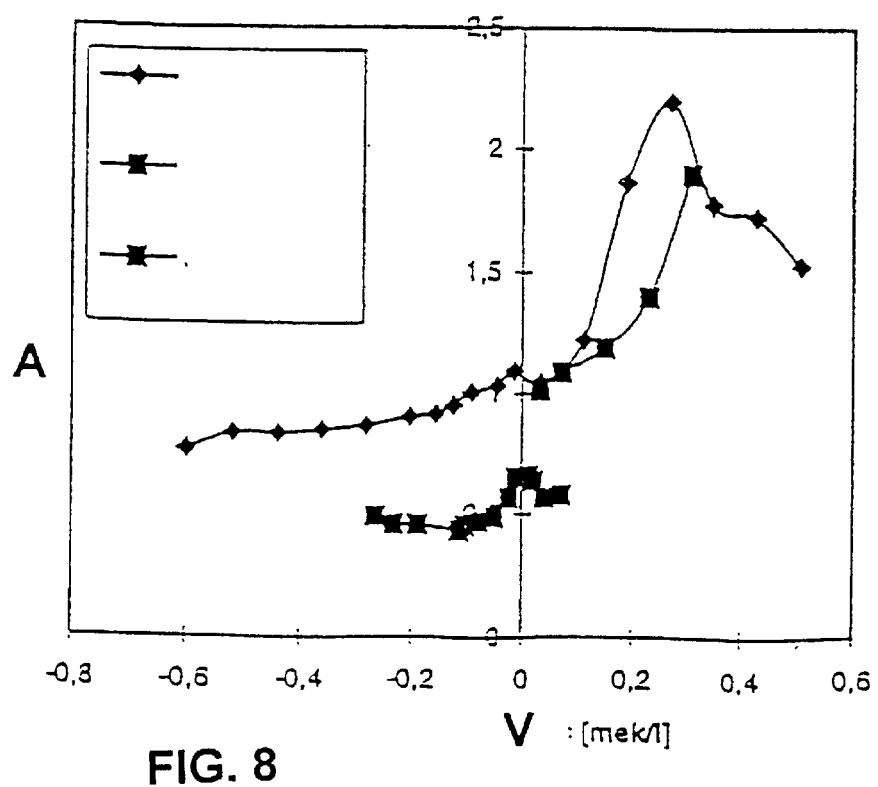

FIG. 8. The curves made from the filtrate of coated reject and the comparison filtrate in the same figure. The upper curve is made from the filtrate, the following curve under that is made from the filtrate on the following day and the lowest curve is the comparison curve. The anionicity/cationicity is on the X-axis, which can be used instead of the charging state.

COMMENTS

The examples show that the method of the invention works well, because the accuracy is good especially at the equivalent point. The method is clean, because the samples do not need to be titrated as often as in the method that is based on titrations only, and the samples do not become neutral so often. In the neutral state, the harmful substances are in a sticky form and might form adhering clods, which they cannot do in the same extent at all in a colloidal form. Thus, in the measurement vessels, the samples are most of the time in colloidal form, when they can not dirty as during the titration. The method is quick, because the measurement of the absorbance with spectrophotometer is muck quicker than a titration.

The differences depend on the existence of colloidal and solid particles in the sample, whereby the penetrating light is spread and thus have an influence also on the absorbance. Also the electrolytes used in the method have an influence on the state of the sample. A negatively charged sample is relatively stabile and stays opaque in spite of long preservations. Additions of cationic agent leads to coagulation, whereby the particles adhere to each other and strive to move to the bottom of the vessel or adhere to the fibers. Such changes in the sample naturally have an influence on the absorbance. The method can be made even more accurate with still another advantageous embodiment by measuring the absorbance against a sample prepared exactly in the same way, to which only water has been added instead of indicator, whereby the result only measures the change that took place in the indicator solution only.

A direct addition of indicator usually does not lead to color changes, but anionic component is added so that, the color of the indicator presents the anionic form of the indicator in the starting position.

What is claimed is:

1. A method for determination of the charging state of filtrates of fiber masses used in the manufacturing of paper and cardboard, characterized by the following steps
   a) an anionic sample is filtrated from fibers through a filter,
   b) indicator color is added to the filtrate,
   c) the absorbance of the filtrate is measured, and
   d) the charging state of the solution is read from an earlier made calibration curve that corresponds to the measured absorbance.

2. The method according to claim 1 wherein the calibration curve is made by means of the following steps
   a) a sufficient amount of samples is taken from the same anionic sample and such different known amounts of cationic agent are added to these samples, that at least a part of the samples are cationic and at least a part of the samples are anionic,
   b) the charging states of the filtrated samples are determined by cationic titration or potentiometric measurements,
   c) the absorbances corresponding to the charging states are measured, and
   d) a calibration curve or table is drawn, wherein a given absorbance corresponds to a given charging state.

3. The method according to claim 1 wherein the calibration curve is made by means of the following steps
   a) a sufficient amount of samples is taken from the same anionic sample and such different known amounts of cationic agent are added to these samples, that at least a part of the samples are cationic and at least a part of the samples are anionic, whereafter the same amount of cationic agent is added to all samples so that all samples are cationic,
   b) the charging states of the filtrated samples are determined by anionic titration,
   c) the absorbances corresponding to the charging states are measured, and
   d) a calibration curve is drawn, wherein a given absorbance corresponds to a given charging state.

4. The method according to claim 1 wherein the absorbance of the sample is corrected by comparing it to a sample prepared in exactly the same way, but in which only water has been added instead of indicator, whereby the result better corresponds only to the change taken place in the indicator solution.

5. The method according to claim 1 wherein the absorbance is measured with spectrophotometer at a wave length within the range of visible light, preferably at the wave length of 500 or 615 nm, most preferably at the wave length 615 nm.

6. The method according to claim 1 wherein the indicator is p-toluidin, which is added as a solution or in solid form in such an amount, that the color change can be seen with the bare eye.

7. The method according to claim 1 wherein the object for the measurement is a filtrate of a mass used as raw material for paper or cardboard, a filtrate of coated reject or some other fiber mass filtrate used in the connection with paper manufacturing.

8. The method according to claim 1 wherein the filtration is carried out with black band paper or the like.

9. The method according to claim 1 wherein the cationic agent is a cationic polymer.

* * * * *